United States Patent
Beden et al.

(10) Patent No.: US 12,005,167 B2
(45) Date of Patent: Jun. 11, 2024

(54) METHOD AND DEVICES FOR THE CALIBRATION OF A PUMP FOR THE BLOOD TREATMENT

(71) Applicant: Fresenius Medical Care Deutschland GmbH, Bad Homburg (DE)

(72) Inventors: Josef Beden, Mainz-Kastel (DE); Juergen Klewinghaus, Oberursel (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 1190 days.

(21) Appl. No.: 16/630,074

(22) PCT Filed: Jul. 6, 2018

(86) PCT No.: PCT/EP2018/068442
§ 371 (c)(1),
(2) Date: Jan. 10, 2020

(87) PCT Pub. No.: WO2019/011822
PCT Pub. Date: Jan. 17, 2019

(65) Prior Publication Data
US 2020/0353140 A1    Nov. 12, 2020

(30) Foreign Application Priority Data
Jul. 10, 2017 (DE) .......................... 102017115429.9

(51) Int. Cl.
*A61M 1/16* (2006.01)
*A61M 1/14* (2006.01)
(Continued)

(52) U.S. Cl.
CPC ............ *A61M 1/1601* (2014.02); *A61M 1/14* (2013.01); *A61M 1/16* (2013.01); *A61M 1/1615* (2014.02);
(Continued)

(58) Field of Classification Search
CPC ........ A61M 1/14; A61M 1/16; A61M 1/1601; A61M 1/1615; A61M 1/1617; A61M 1/34;
(Continued)

(56) References Cited

U.S. PATENT DOCUMENTS 4,670,007 A    6/1987 Wheeldon et al.
4,769,001 A    9/1988 Prince
(Continued)

FOREIGN PATENT DOCUMENTS

CN    103251993    8/2013
CN    103379926    10/2013
(Continued)

OTHER PUBLICATIONS

International Search Report and Written Opinion in Application No. PCT/EP2018/068442, dated Oct. 2, 2018, 5 pages (English Translation).

(Continued)

*Primary Examiner* — John Kim
(74) *Attorney, Agent, or Firm* — Fish & Richardson P.C.

(57) ABSTRACT

The present disclosure relates to a method for determining an actual pump rate and/or for calibrating a blood pump of a blood treatment apparatus connected to an extracorporeal blood circuit. The method includes providing a blood pump of a blood treatment apparatus or establishing a signal communication to a blood pump. The blood pump comprises, or is connected to at least a first source for a fluid and at least a first line of an extracorporeal blood circuit which is connected to the first source downstream. Furthermore, the blood pump comprises, or is connected to, a reception unit for receiving fluids of the first source wherein the reception unit is in fluid communication with the first line. The reception unit is arranged on or at a first weighing (Continued)

device such that the weight of the reception unit or of its content is determined using the weighing device.

15 Claims, 3 Drawing Sheets

(51) Int. Cl.
| | |
|---|---|
| A61M 1/34 | (2006.01) |
| A61M 1/36 | (2006.01) |
| A61M 60/113 | (2021.01) |
| A61M 60/279 | (2021.01) |
| A61M 60/37 | (2021.01) |
| A61M 60/422 | (2021.01) |
| A61M 60/50 | (2021.01) |
| A61M 60/546 | (2021.01) |
| A61M 60/833 | (2021.01) |

(52) U.S. Cl.
CPC ............ *A61M 1/1617* (2014.02); *A61M 1/34* (2013.01); *A61M 1/3621* (2013.01); *A61M 1/3644* (2014.02); *A61M 1/3649* (2014.02); *A61M 1/365* (2014.02); *A61M 60/113* (2021.01); *A61M 60/279* (2021.01); *A61M 60/37* (2021.01); *A61M 60/422* (2021.01); *A61M 60/50* (2021.01); *A61M 60/546* (2021.01); *A61M 60/833* (2021.01); *A61M 1/362264* (2022.05); *A61M 2205/3393* (2013.01); *A61M 2205/70* (2013.01)

(58) Field of Classification Search
CPC .......... A61M 1/3621; A61M 1/362264; A61M 1/3644; A61M 1/3649; A61M 1/365; A61M 60/113; A61M 60/279; A61M 60/37; A61M 60/422; A61M 60/50; A61M 60/546; A61M 60/833; A61M 2205/3393; A61M 2205/70
See application file for complete search history.

(56) References Cited

U.S. PATENT DOCUMENTS

| | | |
|---|---|---|
| 5,200,090 A | 4/1993 | Ford et al. |
| 2010/0168639 A1 | 7/2010 | Cantu et al. |
| 2012/0193290 A1 | 8/2012 | Breuel et al. |
| 2015/0005699 A1 | 1/2015 | Burbank et al. |
| 2016/0121037 A1 | 5/2016 | Golarits et al. |
| 2016/0175511 A1 | 6/2016 | Planas et al. |
| 2018/0333528 A1 | 11/2018 | Klewinghaus |

FOREIGN PATENT DOCUMENTS

| | | |
|---|---|---|
| CN | 105561415 | 5/2016 |
| CN | 105688299 | 6/2016 |
| CN | 105709292 | 6/2016 |
| CN | 106573098 | 4/2017 |
| DE | 3147187 | 6/1983 |
| DE | 10112848 | 9/2001 |
| DE | 102009018664 | 10/2010 |
| DE | 102009024468 | 12/2010 |
| EP | 0321754 | 6/1989 |
| EP | 0403401 | 12/1990 |
| EP | 0723463 | 7/1996 |
| EP | 3031481 | 6/2016 |
| EP | 3031485 | 6/2016 |
| EP | 3034106 | 6/2016 |
| JP | 2000-107281 | 4/2000 |
| WO | WO 91/15253 | 10/1991 |
| WO | WO 93/00120 | 1/1993 |
| WO | WO 95/10310 | 4/1995 |
| WO | WO 96/25214 | 8/1996 |
| WO | WO 99/23386 | 5/1999 |
| WO | WO 2016/057982 | 4/2016 |

OTHER PUBLICATIONS

International Preliminary Report in Application No. PCT/EP2018/068442, dated Jan. 14, 2020, 8 pages (English Translation).

METHOD AND DEVICES FOR THE CALIBRATION OF A PUMP FOR THE BLOOD TREATMENT

CROSS-REFERENCE TO RELATED APPLICATIONS

The present application is the national stage entry of International Patent Application No. PCT/EP2018/068442, filed on Jul. 6, 2018, and claims priority to Application No. DE 10 2017 115 429.9, filed in the Federal Republic of Germany on Jul. 10, 2017, the disclosure of which are express incorporated herein in entirety by reference thereto.

TECHNICAL FIELD

The present disclosure relates to a method for the calibration of a pump for blood treatment. In addition, it relates to a control device, a blood treatment apparatus, a digital storage medium, a computer program product, and a computer program.

BACKGROUND

During extracorporeal blood treatment, blood is removed from the patient and conducted along a blood circuit extracorporeally and through a blood filter. For this purpose, usually a blood pump is utilized.

SUMMARY

The actual pump rate may, in particular when roller pumps are used, deviate from the predefined conveyance rate. The predefined conveyance rate may be predefined e.g. by the rotation speed of the pump rotor.

This disclosure describes a method for the calibration of a pump for blood treatment.

Further, a blood treatment apparatus configured to execute a method is disclosed, and a control device provided for executing the method. A suitable digital storage medium, a suitable computer program product, and a suitable computer program are also disclosed.

The present disclosure relates to a method for determining the actual pump rate (may be volume per time) and/or for the calibration of a blood pump of a blood treatment apparatus, which is connected to an extracorporeal blood circuit.

The method disclosed herein thereby encompasses as the first of several steps, providing a blood pump of a blood treatment apparatus or establishing a signal communication to a blood pump. The blood pump is connected or connectable to at least a first fluid source and to at least a first line of an extracorporeal blood circuit, which is connected downstream of the first source, wherein this first source is preferably not a patient and the fluid from the source is preferably not blood. Further, the blood pump is connected to at least a reception unit for receiving fluids from or of the first source, wherein the reception unit is connected or connectable to the first line in fluid communication. In this, the reception unit is arranged on or at a first weighing device such that the weight of the reception unit and/or the weight of its content may be determined via the weighing device.

The method encompasses as a further step, setting a value for a pump rate being adjustable at the blood pump as a set pump rate or transmitting such value to the blood pump as a set pump rate.

In a next step, the blood pump is operated at the set pump rate during a certain conveyance time period such that the fluid from the source is conveyed as actual volume through the first line, or fluid, that is present in the first line and is displaced by fluid from the source, is conveyed into the reception unit.

In a further step encompassed by the method disclosed herein, an actual volume conveyed during a conveyance time period is determined by the weighing device depending on the change of weight of the reception unit and/or of its content. In this, the density of the conveyed fluid may be considered. Determining the actual volume takes place for example based on the weight of the actual volume conveyed in real or based on a weight change of the reception unit or of its content caused by or due to the conveyed volume, or based on for example known relations between volume and weight of the conveyed fluid.

The method encompasses as a further step, the determining of a mathematical relation between the actual volume and a target volume which target volume results from the conveyance time period and the set pump rate and/or the determining of the real or the actual pump rate from or based on the actual volume and the target volume.

The control or closed-loop device disclosed herein is suitable and provided and/or designed and/or configured to execute the method.

A blood treatment apparatus as disclosed herein comprises or is connected to an extracorporeal blood circuit. The blood treatment apparatus further comprises or is connected to at least one blood pump (it serves for conveying blood during a blood treatment), which is connected to at least a first fluid source and to at least a first line, which is connected downstream of the first fluid source. Furthermore, the blood treatment apparatus comprises or is connected to at least one reception unit for receiving fluid of the first source, wherein the reception unit is in fluid communication with the first line as well as with a first weighing device for the reception unit.

The blood treatment apparatus further comprises or is connected to a control or closed-loop device, which is configured to set a value for a pump rate being adjustable at the blood pump as a user-set pump rate. Further, the control or closed-loop device is configured to operate at least one blood pump at the set pump rate during a certain conveyance time period such that the fluid from the source is conveyed through the first line into the reception unit. In addition, the control or closed-loop device which is connected to the blood treatment apparatus, is configured to determine an actual volume and/or an actual pump rate during the conveyance time period with the aid of the first weighing device. It is further configured to determine a mathematical relation between the actual volume and the target volume, which results from the conveyance time period and the set pump rate.

The blood treatment apparatus is provided and embodied and/or equipped for executing the method.

The control unit as disclosed herein is suitable and provided and/or designed and/or configured to execute the methods disclosed herein in interaction with each device required thereto, as described in the following by way of example.

A digital, particularly a non-volatile storage medium as disclosed herein, particularly a machine-readable data storage device, particularly a disk, CD, EPROM or DVD, with electrically readable control signals may interact with a programmable computer system such that the machine-induced steps of a method are prompted.

In doing so, all, several or some of the machine-induced steps of the method may be prompted.

A computer program product disclosed herein comprises a program code that is volatile or saved on a machine-readable medium for prompting the machine-induced steps of the method when the computer program product runs on a computer. A computer program product can be understood as, for example, a computer program which is stored on a storage device, an embedded system as a comprehensive system with a computer program (for example, an electronic device with a computer program), a network of computer-implemented computer programs (for example, a client-server system, a cloud computing system, etc.), or a computer on which a computer product is loaded, executed, saved or developed.

The term machine-readable medium as used herein denotes in certain embodiments a medium containing data or information which is interpretable by software and/or hardware. The medium may be a data medium, like a disk, a CD, DVD, a USB stick, a flashcard, an SD card or the like.

A computer program comprises a program code for prompting the machine-induced steps of a method when the computer program runs on a computer. A computer program can be understood as, for example, a physical, ready-for-distribution software product which comprises a computer program.

It also applies for the computer program product and for the computer program that all, several or some of the machine-induced steps of the method are prompted.

Embodiments may comprise some, several or all of the following features in arbitrary combination as long as this is not recognized by the skilled person to be technically impossible. Advantageous developments are each also subject-matter of the dependent claims.

In all of the embodiments herein, the use of the expression "may be" and "may have" etc. is synonymous to "is preferably" or "has preferably," etc. respectively, and is intended to illustrate embodiments.

Whenever numerical words are mentioned herein, the person skilled in the art will comprehend them as indications of numerical lower limits. Unless it leads the person skilled in the art to an evident contradiction, the person skilled in the art will comprehend the specification for example of "one" as encompassing "at least one". This understanding is also equally encompassed by the present invention as the interpretation that a numeric word, for example, "one" may alternatively mean "exactly one", wherever this is evidently technically possible for the person skilled in the art. Both are encompassed by the present invention and apply herein to all used numerical words.

Whenever an embodiment is mentioned herein, it represents an exemplary embodiment of the present disclosure.

In certain exemplary embodiments, the blood treatment apparatus is a hemodialysis apparatus, hemofiltration apparatus or hemodiafiltration apparatus, in particular an apparatus for chronic renal replacement therapy or for the continuous renal replacement therapy (CRRT).

In some embodiments, the blood treatment apparatus comprises a control or closed-loop device, preferably. The control or closed-loop device may be programmed and/or configured to execute the method in interaction with other devices, in particular a blood treatment apparatus.

The extracorporeal blood circuit is in certain embodiments a tube set. The extracorporeal blood circuit is anyhow provided for extracorporeally conducting a patient's blood, for example, by hemodialysis, hemofiltration, hemodiafiltration or the like.

In some embodiments, the extracorporeal blood circuit is embodied, at least in sections, as an integral and possibly a non-detachable part of the blood cassette, in others it is not. Thus, a freely movable tube section of the extracorporeal blood circuit may continue or extend in one piece or integrally on or in the functional device, for example, a blood cassette, and vice versa.

A blood cassette is in certain embodiments a device which is used in a blood treatment.

Examples of blood cassettes include disposables or single-use blood cassettes.

Exemplary embodiments of a blood cassette are disclosed in the application of the Applicant with the publication number DE 10 2009 018 664 A1 having the title "Externe Funktionseinrichtung, Blutbehandlungsvorrichtung zum Aufnehmen einer erfindungsgemäßen externen Funktionseinrichtung, sowie Verfahren", which was submitted to the German Patent and Trademark Office on 23 Apr. 2009, and in the application of the Applicant with the publication number DE 10 2009 024 468 A1 of the same title, which was submitted to the German Patent and Trademark Office on 10 Jun. 2009. The respective disclosures of these two applications are herewith fully incorporated by way of reference.

The arterial line section of the extracorporeal blood circuit is in certain embodiments the line section into which the patient's blood that leaves the body of the patient for the purpose of the extracorporeal blood treatment flows, and in which said patient's blood is present before entering the blood treatment device, for example, a dialyzer.

In certain embodiments, the first section of the arterial line section is or encompasses the arterial needle connection to the patient, for example, through the arterial needle connection in a double-needle dialysis method.

In some embodiments, the method encompasses a step which determines a relation between the set pump rate and the actual pump rate. In this, the actual pump rate is determined in consideration of the actual volume and the conveyance time period.

In some embodiments, a correction factor or a calibration factor for the blood pump is defined during/by the method. It is defined, calculated or determined based on the relation between the pump rate being adjusted at the blood pump and the actual pump rate and/or based on the actual volume and the target volume.

In some embodiments, generating the same pressure relations before and after conveyance (or conveyance time period) and/or during conveyance (or conveyance time period) in the first line is considered as a further step of the method. The designation "after conveyance", may thereby describe a point of time before determining the actual volume and/or the actual pump rate.

The "same pressure relations during conveyance" may be understood that two, three or more measurements, which are made during the conveyance time period, lead to the same results or to results which are considered to be the same (since they may be due to measurement fluctuations). Alternatively, one may understand here that the measured pressure does not change at least over a time segment of the conveyance time period or a time period within the conveyance time period, or over the total conveyance time period.

In some embodiments, the extracorporeal blood circuit comprises a blood filter or a dialyzer, which comprises or is connected to a mostly semi-permeably membrane.

In some embodiments, the reception unit is in fluid communication with the first line.

In some embodiments, the reception unit is downstream of the blood filter or the dialyzer and is in fluid communication with the first line through the membrane of the blood filter or dialyzer.

In some embodiments of the method, the blood filter or the dialyzer is connected to a dialysis liquid inlet line and to a dialysate line. An effluent pump may be arranged in the dialysate line. In this, a check valve and/or an occluding pump may be integrated into the dialysis liquid inlet line. The check valve preferably serves to prevent an undesired flow in the direction opposite to the flow direction of the dialysis liquid inlet line during use as intended and/or in the direction away from the blood filter.

In some embodiments, the blood filter or the dialyzer is in fluid communication with an arterial patient line and with a venous patient line, wherein a tube clamp is arranged in or on the venous patient line. In this, the method further encompasses closing the tube clamp at the venous patient line during the conveyance time period and/or executing the methods disclosed herein.

In some embodiments of the method, the blood pump and an effluent pump convey at the same pump rate during the conveyance time period.

The effluent pump may be a pump for discarding spent dialysate from the blood filter or may be a filtrate pump.

In some embodiments, the method encompasses a step of generating the same pressure relation in the first line before and after the conveyance time period and/or controlling the pump at a constant pressure in the first line during the conveyance time period.

In certain embodiments, the effluent pump is rotated to generate the same pressure relation, in particular through the control or closed-loop device, in particular in a pressure-controlled manner.

In some embodiments, the first fluid is a saline solution, a dialysis liquid or a substituat, in particular a priming liquid.

In some embodiments, the method encompasses the step of providing the blood treatment apparatus as a hemodialysis apparatus, hemofiltration apparatus or hemodiafiltration apparatus, in particular as an apparatus for chronic renal replacement therapy or for the continuous renal replacement therapy (CRRT).

The venous line section of the extracorporeal blood circuit is in some embodiments the line section from which the extracorporeally treated patient's blood flows towards or back into the body of the patient after its treatment in a blood treatment device, for example, a dialyzer.

The control device is in some embodiments embodied as a closed-loop device.

The blood treatment apparatus comprises in certain embodiments at least one control device.

Preferably, the method is not executed during a patient's treatment. Preferably, the method is executed without connecting the blood treatment apparatus to a patient. Preferably, the method is executed without having taken or without taking blood from the patient and/or preferably without returning blood to the patient.

For example, methods which are based on the number of pumping movements of the blood pumps, for example, the number of rotations of their rotor, are considered as methods for realizing a set value for a pump rate adjustable at the blood pump as a set pump rate.

Some or all embodiments may comprise one, several or all of the advantages named above and/or hereafter.

One advantage achievable by some of the embodiments disclosed herein is that the blood conveyance rate may be accurately ascertained by the blood pump. This may be particularly important for the treatment of the patient. Drugs are dosed into the patient depending on the blood conveyance rate, for example in the case of regional anticoagulation, in which citrate is added into the flowing blood in certain proportions depending on the blood flow. Knowing the exact blood conveyance rate is of particular advantage here. The same applies for cases in which only little blood flows are generated by the blood pump, like in pediatric applications. It is here important to know the blood conveyance rate particularly precisely.

A further advantage may be to be able to omit the provision and use of flow sensors for determining the exact blood flow. The exact blood flow is known—at least sufficiently accurately—when the exact blood conveyance rate of the blood pump is known.

Another further advantage may be that in some embodiments, the weighing devices used for weighing the reception unit in order to determine the actual volume are the weighing devices which are available or present, because they are used for balancing after the completion of a blood treatment executed according to the method, in particular in the continuous renal replacement therapy (CART).

In this, a particular advantage may be that the blood pump calibrates automatically and/or the correction factor may be automatically determined. For this purpose, no transfer or arrangement of fluid containers, for example such that they lie on the weighing devices, no provision of fluid containers specially provided for calibration, etc. is required. Thus, work and time may be saved in certain embodiments. Advantageously, arrangements may be considered which are used without changes in the subsequent blood treatment.

The actual pump rate may, in particular when roller pumps are used, deviate from the predefined conveyance rate, such that pump rate calibration is advantageous to eliminate or reduce such deviations. The predefined conveyance rate may be predefined by the rotation speed of the pump rotor.

BRIEF DESCRIPTION OF THE DRAWINGS

In the following, the present invention is merely exemplarily described with regard to the enclosed drawings, in which identical reference numerals refer to the same or similar components. The following applies.

DETAILED DESCRIPTION OF THE DRAWINGS

Figure 1:
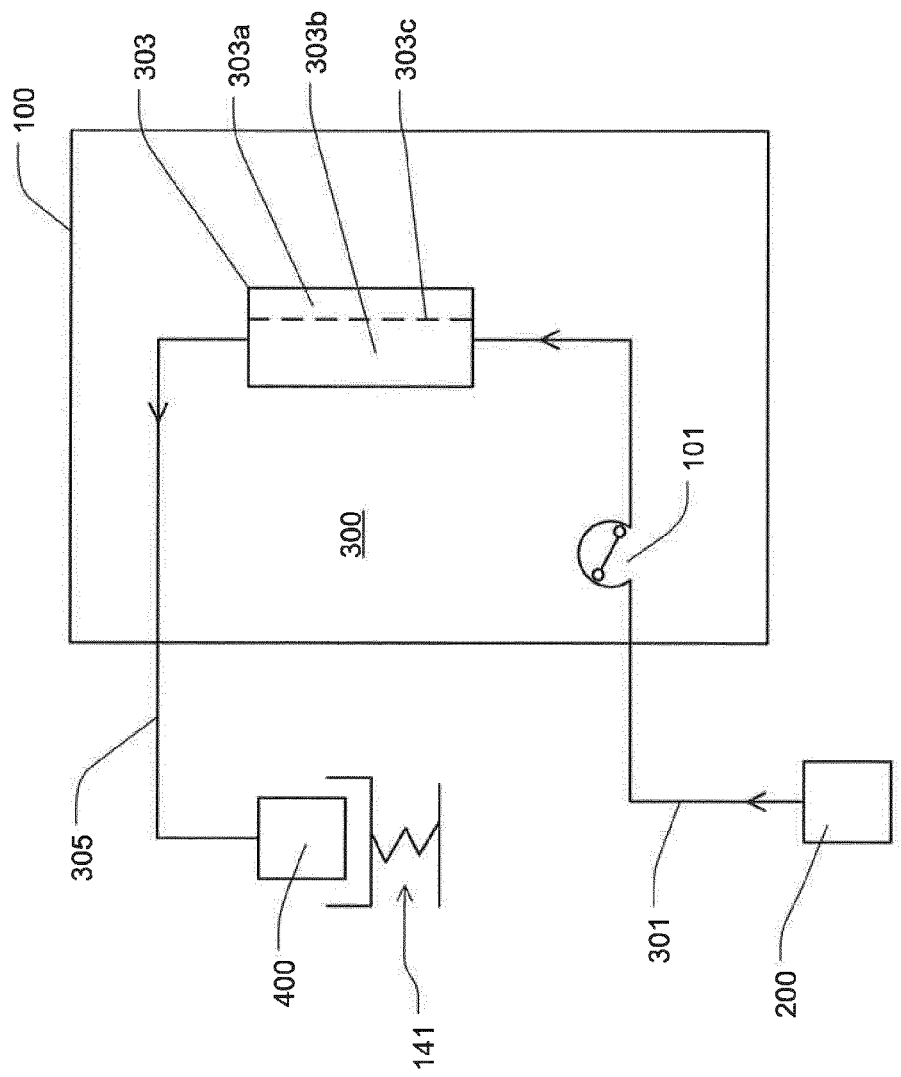
FIG. 1 shows a simplified illustration of a blood treatment apparatus with an extracorporeal blood circuit in a first embodiment.

FIG. 1 shows a simplified illustration of a blood treatment apparatus 100 connected to an extracorporeal blood circuit 300 during the execution of the method described herein. FIG. 1 shows the basic principle.

The extracorporeal blood circuit 300 comprises a first line 301, here being an arterial line section.

The first line 301 is in fluid communication with a blood treatment device, here exemplarily a blood filter 303 or a dialyzer. The blood filter 303 comprises a dialysis liquid chamber 303a and a blood chamber 303b which are separated from each other by a mostly semi-permeable membrane 303c.

The extracorporeal blood circuit 300 further comprises at least a second line 305, here being a venous line section.

Both the first line 301 and the second line 305 may serve for the connection to the vascular system of the patient, not shown.

The blood treatment apparatus 100, represented in FIG. 1 only through some of its devices by means of which the method, described herein, is executed, comprises a blood pump 101. During the treatment of the patient, the blood pump 101 conveys blood through sections of the extracorporeal blood circuit 300 and in direction towards the blood filter 303, as the small arrow tips show, which generally indicate the flow direction in the figures.

For calibrating the blood pump 101, fluid from a first source 200 is pumped by a blood pump 101, which may optionally be embodied as a roller pump or as any other occluding pump, along the first line 301 in direction of the reception unit 400.

The source 200 may be, for example, a bag or a container. The same applies for the reception unit 400. The source 200 may further be a fluid line, from which online and/or continuously produced or mixed liquid is provided, for example, a hydraulic outlet or hydraulic port of the blood treatment apparatus The reception unit 400 is connected to a first weighing device 141 for weighing the weight of the reception unit 400 or of the fluid received therein or for determining a weight change. For example, the reception unit 400 may be disposed as a collecting bag on a weighing surface of the first weighing device 141 or may hang on a weighing hook.

If the blood pump 101 now conveys over a predetermined or determinable time period, namely the conveyance time period T then, based on the pump rate P1 of the blood pump 101 determined by the user or by a test program and the conveyance time period T, the volume of the fluid which should have been conveyed, if the blood pump 101 would indeed convey at the predetermined pump rate P1, may be determined by the simple relation $P1*T=VS$.

In practice, the actually conveyed volume, which is herein referred to as actual volume VI may deviate from the target volume.

The actual volume VI is however found again in the reception unit 400 after termination of the conveyance time period T. The actual volume can be determined based on the weight measurement, which is herein exemplarily carried out by the first weighing device 141; the weight of the actual volume corresponds to the increase of the weight of the reception unit between a measurement made before the beginning of the conveyance time period T and a measurement made at a point of time which is after the conveyance time period T.

A comparison of the measured actual volume VI with the calculated target volume VS may serve for calculating a correction factor or a calibration value of the set pump rate or of the blood pump 101.

Figure 2:
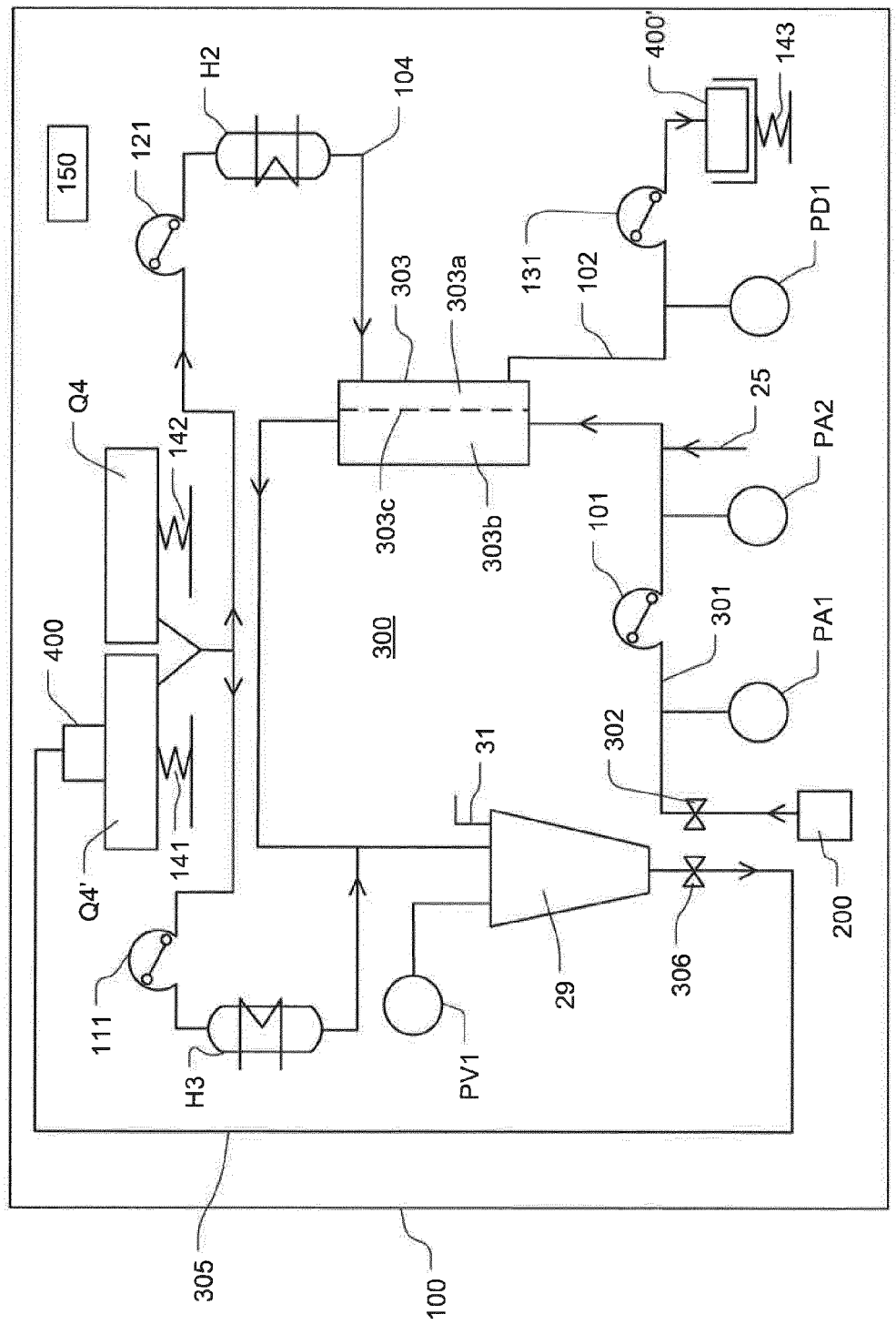
FIG. 2 shows a simplified illustration of a blood treatment apparatus with an extracorporeal blood circuit in a second embodiment.

A control or closed-loop device 150, first described and shown in FIG. 2 (see FIG. 2), may be configured to execute the foregoing method. Optionally, an automatic execution takes place. Optionally, the execution starts automatically, for example within a test function, a self-check when starting the blood treatment apparatus during or following a priming process, etc.

FIG. 2 shows a simplified illustration of a blood treatment apparatus 100 with an extracorporeal blood circuit 300 in a second embodiment.

In addition to the aforementioned blood pump 101, the arrangement shown in FIG. 2 further comprises a number of other, each being optional, pumps, i.e. the pump 111 for substituat, the pump 121 for dialysis liquid and the pump 131 for dialysate and/or effluent.

The pump 121 is provided to pump dialysis liquid out of a source Q4, for example, a bag, and to convey said dialysis liquid via a dialysis liquid inlet line 104 through an optionally available bag heating with a bag H2.

The dialysis liquid conveyed in this way, leaves again through a dialysate line 102, supported by the pump 131, and may be discarded.

An optional arterial sensor PA1 is provided upstream of the blood pump 101. Sensor PA1 measures the pressure in the arterial line during a treatment of a patient.

A further optional pressure sensor PA2 is provided downstream of the blood pump 101, however upstream of the blood filter 303 and, if provided, upstream of an addition site 25 for heparin. Pressure sensor PA2 measures the pressure upstream of the blood filter 303 ("pre-hemofilter").

An again further pressure sensor may be provided as PD1 downstream of the blood filter 303, however preferably upstream of the pump 131 in the dialysate line 102, to measure a filter pressure downstream of the blood filter 303.

Blood, which leaves the blood filter 303, flows through or perfuses an optional venous blood chamber 29, which may comprise an optional closable ventilation device 31 and which may be in fluid communication with a further pressure sensor PV1.

In the example of FIG. 2, the source Q4 and an optional further source Q4', out of which substituat is collected via the pump 111 through a further bag heating with bag H3, as well as the caught or discarded dialysate are optionally subject to balancing. For the purpose of balancing, two further optional weighing devices 142 and 143 are provided in addition to the first weighing device 141 known from FIG. 1.

The balancing shown herein exemplarily corresponds to a gravimetric balancing, but may also encompass any other balancing, for example using balancing chambers.

The arrangement shown exemplarily in FIG. 2 comprises a control or closed-loop device 150. for controlling the blood treatment apparatus 100 It may be in a wired or wireless signal communication with each of the components mentioned herein—in any case or in particular with the blood pump 101. It may be optionally configured to execute the method described herein.

The first line 301 is optionally connected to tube clamp 302 for locking or closing the line 301. The second line 305 is optionally connected to a tube clamp 306 for locking or closing the line 305.

Even though the embodiment of FIG. 2 is shown with a reception unit 400 for fluid the weight of which is determined by the first weighing device 141, wherein the reception unit 400 may be arranged to the blood side due to its fluid communication with the blood circuit, here downstream of the blood filter 303.

However, the reception unit may alternatively be arranged on the hydraulic side or filtrate side (i.e., not on the blood side, rather in the area of the component 102 and 131). In this way, the reception unit may be weighed by a third weighing device 143, as indicated with the reference numeral 400'.

Figure 3:
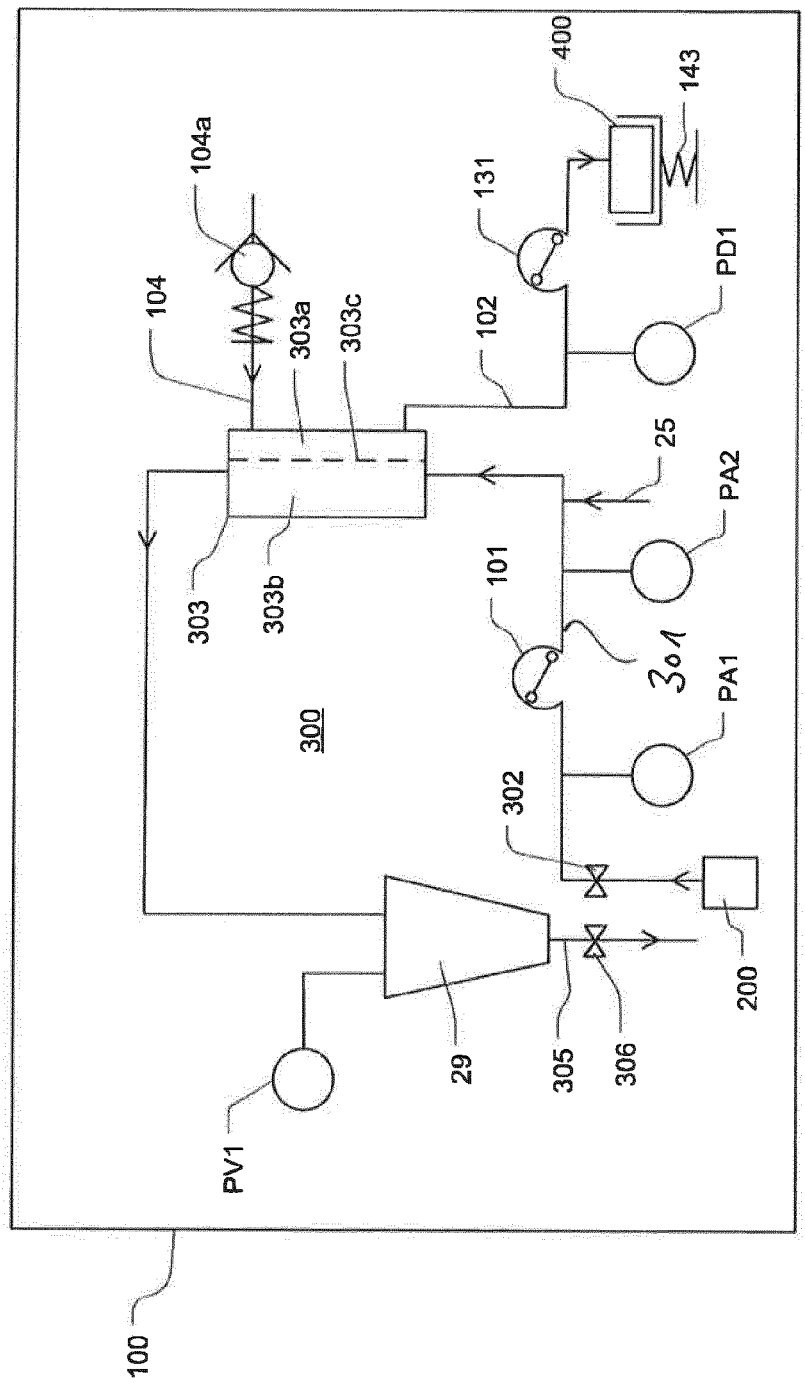
FIG. 3 shows a simplified illustration of a blood treatment apparatus with an extracorporeal blood circuit in a third embodiment.

FIG. 3 shows a simplified illustration of a blood treatment apparatus 100 with an extracorporeal blood circuit 300 in a third embodiment.

The illustration of FIG. 3 differs from that of FIG. 2 already by the fact that a number of components, which are shown in FIG. 2 for the sake of clarity, are not shown again in FIG. 3. However, they may also optionally be present here.

The embodiment shown in FIG. 3 differs however from that of FIG. 2 in that an optional check valve 104a is arranged in the dialysis liquid inlet line 104. The check valve 104a opens at a corresponding high pressure to enable a flow through the dialysis liquid inlet line 104 in direction of the blood filter 303. However, the check valve 104a prevents a flow in the opposite direction through the dialysis liquid inlet line 104.

In the embodiment of FIG. 3, the blood pump 101 conveys fluid from the source 200 into the blood filter 303. Since the tube clamp 306 of the second line 305 is closed, the fluid conveyed passes through the membrane 303c from the blood chamber 303b into the dialysis liquid chamber 303a. The check valve 104a—or another occluding device, for example, a roller pump instead of the check valve or in addition thereto—prevents that the fluid passing into or through the dialysis liquid chamber 303a leaves the latter through a line other than the line 102. Conveying the fluid along the aforementioned path is ensured by the pumping function of the pump 131, the effluent pump, inserted into the dialysate line 102. Finally, the fluid is forwarded into the reception unit 400 whose weight change may be determined by the third weighing device 143. As a result, the actual volume VI, which was conveyed by the blood pump 101 during the conveyance time period T, is obtained.

The following features, although not shown in the figures, may again in each embodiment be purely optional and provided in any combination:

The first line 301 may comprise an arterial septum, optionally in form of an addition device.

The first line 301 and/or the second line 305 may comprise an air bubble detector/optical sensor.

The blood circuit may at least partially comprise, be or be connected to, part of a blood cassette, which comprises a hard part covered completely or partially by a film.

LIST OF REFERENCE NUMERALS 25 addition site for heparin (optional)
29 venous blood chamber (optional)
31 ventilation device
100 blood treatment apparatus
101 blood pump
102 dialysate line
104 dialysis liquid inlet or supply line
104a check valve
111 pump for substituat
121 pump for dialysis liquid
131 pump for dialysate and/or effluent
141 first weighing device
142 second weighing device
143 third weighing device
150 control or closed-loop device
200 fluid source
300 extracorporeal blood circuit
301 first line (arterial line section)
302 tube clamp
303 blood filter or dialyzer
303a dialysis liquid chamber
303b blood chamber
303c semi-permeable membrane
305 second line (venous line section)
306 tube clamp
400 reception unit for fluid
400' reception unit for fluid
H2 bag heater with bag (dialysis liquid)
H3 bag heating with bag (substituate)
PA1, PA2 arterial pressure sensor (optional)
PD1 pressure sensor for measuring the filter pressure
PV1 pressure sensor (optional)
P1 set pump rate
Q4 source with dialysis liquid
Q4' source (substituate), optional
T conveyance time period
VI actual volume
VS target volume

The invention claimed is:

1. A method for determining an actual pump rate or for calibrating a blood pump of a blood treatment apparatus connected to an extracorporeal blood circuit, the method comprising:
   providing a blood pump of a blood treatment apparatus, or establishing a signal connection to a blood pump, the blood pump connected to comprising:
      at least a first fluid source;
      at least a first line of an extracorporeal blood circuit which is connected downstream to the first fluid source; and
      at least one reception unit for receiving fluid of the first fluid source, wherein the reception unit is in fluid communication with the first line,
      wherein the reception unit is arranged on or at a first weighing device such that a weight of at least one of the reception unit or of a content of the reception unit is determinable via the first weighing device;
   setting a value for a pump rate being adjustable at the blood pump as a set pump rate, or transmitting such a value to the blood pump as a set pump rate;
   operating the blood pump at the set pump rate during a conveyance time period such that the fluid from the first fluid source is conveyed as actual volume through the first line into the reception unit;
   determining via the first weighing device an actual volume conveyed during the conveyance time period based on a change of the weight of the reception unit or of the contents of the reception unit; and
   determining a mathematical relation between the actual volume and a target volume, the target volume resulting from the conveyance time period and the set pump rate;
   wherein the blood treatment apparatus is configured to maintain a particular pressure within the first line before the conveyance time period and to maintain the particular pressure within the first line after the conveyance time period.

2. The method according to claim 1, wherein the method further comprises:
   determining a relation between the set pump rate and an actual pump rate, wherein the actual pump rate is determined considering the actual volume and the conveyance time period.

3. The method according to claim 2, wherein the method further comprises:
   defining a correction factor or calibration factor for the blood pump based on the relation between the pump rate set at the blood pump and the actual pump rate or based on the actual volume and the target volume.

4. The method according to claim 2, wherein the method further comprises:
   defining a correction factor or calibration factor for the blood pump based on the relation between the pump rate set at the blood pump and the actual pump rate and based on the actual volume and the target volume.

5. The method according to claim 1, wherein:
the blood treatment apparatus is configured to maintain the particular pressure within the first line during the conveyance time period.

6. The method according to claim 1, wherein the extracorporeal blood circuit comprises, or is connected to, a blood filter or a dialyzer that comprises a semi-permeable membrane.

7. The method according to claim 6, wherein the reception unit is in fluid communication with the first line downstream of the blood filter or the dialyzer.

8. The method according to claim 6, wherein the reception unit is in fluid communication with the first line downstream of the blood filter or the dialyzer and through the semi-permeable membrane of the dialyzer.

9. The method according to claim 6, wherein the blood filter or the dialyzer is connected to a dialysis liquid inlet line and a dialysate line, wherein at least one of a check valve and an occluding pump is integrated in the dialysis liquid inlet line to prevent an undesired flow in direction against a flow direction of the dialysis liquid inlet line and/or in direction away from the blood filter.

10. The method according to claim 6, wherein the blood filter or the dialyzer is in fluid communication with an arterial patient line and with a venous patient line, wherein a tube clamp is arranged in or at the venous patient line, wherein the method further comprises:
closing the tube clamp at the venous patient line during the conveyance time period.

11. The method according to claim 1, wherein the blood pump and an effluent pump each convey at a same pump rate during the conveyance time period.

12. The method according to claim 11, wherein:
the blood treatment apparatus is configured to maintain the particular pressure within the first line during the conveyance time period.

13. The method according to claim 1, wherein in order to maintain the particular pressure within the first line, an effluent pump is rotated by a control or closed-loop device, in a pressure-controlled manner.

14. The method according to claim 1, wherein the fluid is a saline solution, a dialysis liquid, a substitute, or a priming liquid.

15. The method according to claim 1 further comprising:
providing the blood treatment apparatus as or being a hemodialysis apparatus, hemofiltration apparatus, or hemodiafiltration apparatus.

* * * * *